United States Patent [19]

Leach, deceased et al.

[11] 4,192,896

[45] Mar. 11, 1980

[54] METHOD OF USING DIALKYLPHENOLS IN THE TREATMENT OF MYCOPLASMA DISEASES

[76] Inventors: Byron E. Leach, deceased, late of Memphis, Tenn.; by Ellanor L. L. Leach, executrix, 1550 N. Parkway #115, Memphis, Tenn. 38112

[21] Appl. No.: 23,254

[22] Filed: Mar. 23, 1979

[51] Int. Cl.$^2$ ............................................. A61K 31/05
[52] U.S. Cl. ................................................... 424/346
[58] Field of Search ........................................ 424/346

[56] References Cited

PUBLICATIONS

Chemical Abstracts 85:14611s, 1976.

*Primary Examiner*—Jerome D. Goldberg
*Attorney, Agent, or Firm*—Cushman, Darby & Cushman

[57] ABSTRACT

2,4-dimethylphenol, and other dialkylphenols, administered in the $10^{-5}$ to $10^{-11}$ molar range are used to prevent or ameliorate the effects of *Mycoplasma pneumoniae* and related microorganisms.

2 Claims, No Drawings

METHOD OF USING DIALKYLPHENOLS IN THE TREATMENT OF MYCOPLASMA DISEASES

DESCRIPTION OF THE INVENTION

The present invention relates to the use of substituted phenols in ameliorating the effects of and preventing mycoplasmal infections. The invention is more particularly concerned with new uses and applications compounds of the general formula:

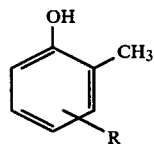

Formula I when R is lower alkyl, to systems containing either *Mycoplasma pulmonis* organisms or mixtures of microorganisms of this type when used in concentrations in the $10^{-5}$ to $10^{-11}$ molar range. The preferred compound is 2,4-dimethylphenol.

It has been found that compounds of Formula I, above, and the pharmacologically acceptable salts thereof, when administered at levels in the $10^{-5}$ to $10^{-11}$ molar range to a system containing mycoplasmal cells, prevent the cytotoxic effects of mycoplasma infections, in vitro, and reduce or eliminate the symptoms which usually accompany mycoplasmal respiratory disease, in vivo.

As to the compounds of Formula I there may be mentioned lower alkyl groups having from 1 to 5 carbon atoms, and preferably R is methyl, such as 2,3-dimethylphenol, 2,4-dimethylphenol, 2,5-dimethylphenol, and 2,6-dimethylphenol; the preferred phenol is 2,4-dimethylphenol. These phenol derivatives have been described many times in the literature as compounds known per se and their methods of preparation are well known in the art. Further, many of these compounds are readily available in commerce. However, as far as can be determined, the use of these compounds by themselves, or as the essential active ingredient in combination with a pharmaceutical carrier or diluent, have never been heretofore described and identified as effecting mycoplasma infections.

As an alternate source of certain compounds embraced in Formula I, the products described in patents U.S. Pat. Nos. 2,989,441 issued June 20, 1961 and 3,421,981, issued Jan. 14, 1969 may be used.

The present invention is based on the discovery that these compounds are effective in preventing or ameliorating the effects of mycoplasmal growths and infections. The compounds of Formula I are particularly effective with mycoplasmal organisms as *Mycoplasma pneumoniae*, especially as in tracheal tissue, as will be more fully discussed and described below.

The antiplasmal compositions of the present invention can be administered orally or intra-nasally and possibly as oral solid compositions such as capsules, tablets and pills which contain the appropriate amount of the compound of Formula I and/or a pharmaceutically acceptable salt thereof per dosage unit. The solid compositions for oral administration and liquid preparations for oral use are prepared in such a manner that the tissues or animal will be exposed to and treated with a compound of Formula I in a molar concentration in the range of $10^{-5}$ to $10^{-11}$. As an illustration, a small quantity of the compound may be placed on cotton in an open container such that the active material will vaporize slowly into the atmosphere of a closed room. A preferred method of administration is including the requisite compound in the drinking water of the animal to be treated.

Another aspect of this invention includes the treatment of laboratory animals, expecially rats, with a preferred compound of my invention, 2,4-dimethylphenol (2,4-DMP) in the treatment of chronic respiratory disease (CRD) caused by *Mycoplasma pulmonis*. This disease is particularly troublesome to the commercial supplies of laboratory animals often destroying entire colonies of susceptible rats. In this procedure, the 2,4-dimethylphenol is conveniently administered in the drinking water of the animals.

The present invention is further described with reference to but not limited by the following Examples.

EXAMPLES OF THE INVENTION

Tracheal organ cultures provide an excellent system for studying interactions between upper respiratory epithelieal cells and various bacterial and viral pathogens. The progress of the infective process can be monitored by observing changes in ciliary activity, necrosis, and thinning of the epithelium. Further, infection, or the lack thereof, may be ascribed to alterations in a single, defined parameter.

Hamster tracheal organ cultures have been used extensively to study the pathogenesis of *Mycoplasma pneumonia;* see "Hamster Tracheal Organ Cultures", Tissue Culture Association Manual, V. J. Evans, V. P. Terry and M. M. Vincent, editors, Vol. 1, pp. 75–80 (1975), Tissue Culture Association, Rockville, Md. *Mycoplasma pneumoniae,* the only mycoplasma conclusively proven to cause respiratory disease in man, elicits pneumonia-like symptoms in hamsters and has been shown to infect and destroy hamster tracheal explants. See Infection and Immunity, Vol. 16, No. 3, pp. 766–772, June 1977; Applied and Environmental Microbiology, Vol. 31, No. 6, pp. 986–989, June, 1976; Journal of Infectious Diseases, Vol. 135, No. 1, pp. 9–19, January, 1977; and Infection and Immunity, Vol. 13, No. 1, pp. 84–91, January, 1976. The infective process apparently starts with the neuraminidase sensitive attachment of the organism to ciliated epithelial cells, followed by the fusion of their plasma membranes. Host cell death results within a matter of hours due to the disruption of adenine dependent energy metabolism.

The following materials and methods were used:

Adult golden hamsters (approximately 140 g. male and female) were used as the tissue source. Animals appearing to be disease-free were selected. Tracheas were removed aseptically and sliced into rings. The rings were rinsed and then transferred into sterile Petri dishes containing a shallow layer of minimal essential medium (MEM, with glutamine, $NaHCO_3$, 10% horse serum and 500 units of penicillin G/ml). These organ cultures were incubated for 24 hours at 36° C. in 5% carbon dioxide and then scored for "relative activity" (RA), a measure of explant viability. "Relative Activity" (0 to 300) is the product of the percentage of the epithelial layer which is intact (0 to 100) and the relative vigor of ciliary beating (0 to 3). Only rings exhibiting RA's of 270 and above were selected for use in these experiments.

The trachea rings were infected with *M. pneumonia*, strain PI 1428 (originally obtained from Dr. Robert Chanock, National Institutes of Health, Bethesda, Md.) which was used in the 10th to 12th passage and was grown on G-199 medium. Tracheal explants were infected with logarithmically growing cells using methods described by Gabridge, et al. Except where otherwise noted, groups of from 3 to 6 rings were preincubated for one hour in MEM with or without an appropriate amount of 2,4-dimethylphenol prior to the addition of mycoplasmas. Following exposure to *M. pneumoniae* for two hours, the rings were rinsed twice in phosphate buffered saline and then placed in a sterile Petri dish containing MEM and, where indicated, the required amount of 2,4-dimethylphenol or 2,4-DMP as used herein. Cultures were incubated at 36° in 5% carbon dioxide and scored daily for RA.

Before undertaking further studies the determination of the toxicity of 2,4-DMP toward hamster tracheal explants and *Mycoplasma pneumoniae* is necessary. Table 1 shows the results of incubating uninfected tracheal rings in various concentrations of 2,4-DMP.

TABLE 1
EFFECTS OF 2,4-DMP ON UNINFECTED HAMSTER TRACHEAL EXPLANTS

| 2,4-DMP (moles/liter) | Relative activity following days of incubation with 2,4-DMP | | | | | | |
|---|---|---|---|---|---|---|---|
| | 1 | 2 | 3 | 4 | 5 | 6 | 7 |
| control no 2,4-DMP | 270 ± 0 | 270 ± 0 | 265 ± 12 | 265 ± 12 | 260 ± 16 | 260 ± 16 | 260 ± 16 |
| $10^{-3}$ | 210 ± 19 | 155 ± 12 | 105 ± 16 | 75 ± 16 | 55 ± 12 | 50 ± 16 | 50 ± 16 |
| $10^{-4}$ | 255 ± 16 | 240 ± 33 | 200 ± 49 | 160 ± 45 | 150 ± 27 | 140 ± 24 | 135 ± 16 |
| $10^{-5}$ | 265 ± 12 | 270 ± 0 | 264 ± 13 | 270 ± 0 | 264 ± 13 | 258 ± 16 | 252 ± 16 |

Significant reductions in RAs are seen at $10^{-3}$ and $10^{-4}$ M. Electron microscopic and histopathic examination of these tissues confirm the destruction of their epithelium. However, no overt cytotoxic effects are evident in rings exposed to 2,4-DMP at $10^{-5}$ M or less.

Similar studies with logarithmic phase cultures of *M. pneumoniae* growing in liquid culture are presented in Table 2. As with the explant tissues, higher concentrations ($10^{-3}$ M) inhibit mycoplasmal growth while lower amounts ($10^{-5}$ M) appear to have little or no effect on the growth of the organism.

TABLE 2
EFFECTS ON 2,4-DMP ON LOGARITHMICALLY GROWING CULTURES OF M. PNEUMONIAE

| (moles/liter) | CFU*/ml following days of culture with | | | | | | | |
|---|---|---|---|---|---|---|---|---|
| | 0 | 1 | 2 | 3 | 4 | 5 | 6 | 7 |
| control no 2,4-DMP | $2 \times 10^4$ | $3 \times 10^5$ | $6.1 \times 10^6$ | $2.5 \times 10^7$ | $6.3 \times 10^7$ | $5.5 \times 10^7$ | $2.1 \times 10^7$ | $6.2 \times 10^6$ |
| $10^{-3}$ | $2 \times 10^4$ | $5 \times 10^4$ | $6.3 \times 10^4$ | $6.5 \times 10^4$ | $6.7 \times 10^4$ | $4.1 \times 10^4$ | $3.3 \times 10^4$ | $1.5 \times 10^4$ |
| $10^{-5}$ | $2 \times 10^4$ | $1.2 \times 10^5$ | $7.5 \times 10^6$ | $2.5 \times 10^7$ | $6.0 \times 10^7$ | $5.9 \times 0^7$ | $1.5 \times 10^7$ | $4.3 \times 10^6$ |
| $10^{-8}$ | $2 \times 10^4$ | $1.5 \times 10^5$ | $7.2 \times 10^6$ | $2.4 \times 10^7$ | $6.3 \times 10^7$ | $5.2 \times 10^7$ | $1.1 \times 10^7$ | $4.2 \times 10^6$ |

*colony-forming units

Infection Studies: *M. pneumoniae* attaches to the surface (as used herein the surface refers to in luminal epithelial lining) of the tracheal tissue within an hour or two following exposure. Decreases in the vigor of ciliary activity and loss of epithelial cells are evident within 24 to 48 hours post-infection. In most cases, little or no ciliary activity remains by the sixth or seventh day. In contrast, uninfected controls exhibit little loss of ciliary activity or epithelial cells after three weeks in the culture. However, the inclusion of very low concentrations of 2,4-DMP in the culture media of explants exposed to *M. pneumoniae* dramatically alters the usual course of events. See Tables 3 and 4.

TABLE 3

| 2,4 DMP (moles/liter) | Relative Activity Days Following Infection With M. Pneumoniae* | | | | | | |
|---|---|---|---|---|---|---|---|
| | 1 | 2 | 3 | 4 | 5 | 6 | 7 |
| control uninfected no 2,4 DMP | 270 ± 0 | 270 ± 0 | 270 ± 0 | 270 ± | 265 ± 12 | 260 ± 16 | 255 ± 16 |
| control infected no 2,4 DMP | 260 ± 16 | 250 ± 16 | 225 ± 16 | 135 ± 16 | 125 ± 23 | 105 ± 16 | 105 ± 16 |
| $10^{-8}$ | 270 ± 0 | 270 ± 0 | 260 ± 16 | 260 ± 16 | 260 ± 16 | 255 ± 16 | 255 ± 16 |
| $10^{-10}$ | 260 ± 16 | 255 ± 16 | 240 ± 19 | 175 ± 23 | 150 ± 19 | 135 ± 16 | 115 ± 23 |

*M. pneumoniae infecting titer: $6 \times 10^6$ CFU/ml

TABLE 4

| 2,4 DMP (moles/liter) | Relative Activity 7 days post infection | Tetrazolium Reduction 7 days post infection |
|---|---|---|
| control uninfected no 2,4-DMP | 260 ± 16 | 1.013 ± 0.034 |
| control infected no 2,4-DMP | 107 ± 15 | 0.424 ± 0.045 |
| $10^{-6}$ | 255 ± 16 | |
| $10^{-7}$ | 255 ± 16 | |
| $10^{-8}$ | 260 ± 10 | 1.066 ± 0.035 |
| $10^{-9}$ | 263 ± 12 | 1.016 ± 0.029 |
| $10^{-10}$ | 114 ± 22 | 0.543 ± 0.142 |
| $10^{-22}$ | 124 ± 18 | 0.453 ± 0.033 |
| $10^{-14}$ | 125 ± 23 | |

*M. pneumoniae infecting titer: $6 \times 10^6$ CFU/ml

Rings exposed to *M. pneumoniae* in the presence of at least $10^{-9}$ M 2,4-DMP remain indistinguishable from uninfected controls with respect to RA, ability to reduce tetrazolium, and surface morphology. Significantly, 2,4-DMP failed to alter the infectious process at concentrations less than or equal to $10^{-10}$ M.

Time Course: In the studies reported thus far, tracheal explants were pretreated with 2,4-DMP for one hour before exposure to *M. pneumoniae*. Some insight into the nature, that is, the site or mode of action, of this protective phenomenon may be gained by altering the time at which 2,4-DMP is added to the culture media. Indeed, the protective effects are significantly reduced or abolished completely if 2,4-DMP is withheld until attachment is essentially complete, as shown in the following Table.

TABLE 5

| Culture | Time of Addition of 2,4 DMP To Explant Media (hours) | Relative Activity 7 Days Following Infection With M. Pneumoniae* | Tetrazolium Reduction 7 Days Following Infection With M. Pneumoniae (OD/mg) |
|---|---|---|---|
| A | −1 | 268 ± 6 | 1.071 ± 0.065 |
| B | 0 | 268 ± 6 | 1.068 ± 0.050 |
| C | 1 | 265 ± 8 | 1.062 ± 0.039 |
| D | 2 | 220 ± 23 | 0.893 ± 0.055 |
| E | 6 | 188 ± 23 | 0.722 ± 0.032 |
| F | 24 | 98 ± 16 | 0.386 ± 0.030 |
| G | 48 | 95 ± 12 | 0.379 ± 0.051 |
| H | 72 | 92 ± 15 | 0.381 ± 0.048 |
| control uninfected no 2,4 DMP | | 268 ± 6 | 1.073 ± 0.070 |
| control infected no 2,4 DMP | | 81 ± 19 | 0.375 ± 0.045 |

Compare cultures, A, B and C (2,4-DMP present during most or all of the attachment phase) with culture D (2,4-DMP added after rinsing) and cultures E, F, G and H (2,4-DMP added 4, 20, 46, and 70 hours after rinsing, respectively).

Specificity of Action: There are six dimethylphenol isomers (2,3-; 2,4-; 2,5-; 2,6-; 3,4-; and 3,5-). They differ from one another in physical appearance (2,4-DMP is a liquid at room temperature, all the others are solids), melting and boiling points, and solubility. Not surprisingly, they exhibit differing degrees of "protectivity". Under the conditions of these studies and at the concentrations tested, 2,4-DMP is more effective than any of the other isomers in inhibiting or altering the course of the infective process. A substituent in the number two position of the benzene ring appears obligatory for any protection to occur.

What is claimed is:

1. A method of inhibiting the growth of *Mycoplasma pneumoniae* in an animal suffering therefrom, consisting essentially of administering to said animal to 2,4-dimethylphenol in a molar concentration in the range of about $10^{-5}$ to about $10^{-11}$.

2. The method of claim 1 wherein 2,4-dimethylphenol is administered to said animal for a period of time sufficient to ameliorate the effects of *Mycoplasma pneumoniae*.

* * * * *